(12) United States Patent
Hashimoto et al.

(10) Patent No.: US 8,911,374 B2
(45) Date of Patent: Dec. 16, 2014

(54) ULTRASONIC DIAGNOSTIC APPARATUS, DIAGNOSTIC IMAGING APPARATUS, AND PROGRAM

(75) Inventors: Shinichi Hashimoto, Otawara (JP); Yoshitaka Mine, Nasushiobara (JP); Tomohiko Kihara, Okayama (JP); Eiichi Shiki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1060 days.

(21) Appl. No.: 12/361,869

(22) Filed: Jan. 29, 2009

(65) Prior Publication Data

US 2009/0198134 A1 Aug. 6, 2009

(30) Foreign Application Priority Data

Jan. 31, 2008 (JP) .................. 2008-021854

(51) Int. Cl.
*A61B 8/14* (2006.01)
*A61B 8/08* (2006.01)
*A61B 8/00* (2006.01)

(52) U.S. Cl.
CPC ................ *A61B 8/14* (2013.01); *A61B 8/5238* (2013.01); *A61B 8/483* (2013.01); *A61B 8/5246* (2013.01); *A61B 8/5253* (2013.01); *A61B 8/543* (2013.01); *A61B 8/0883* (2013.01)
USPC ............ 600/443; 600/437; 382/128; 382/168

(58) Field of Classification Search
None
See application file for complete search history.

(56) References Cited

U.S. PATENT DOCUMENTS

| 6,416,477 | B1 * | 7/2002 | Jago .............................. 600/447 |
| 6,423,004 | B1 * | 7/2002 | Dong et al. .................. 600/443 |
| 6,432,054 | B1 * | 8/2002 | Ustuner et al. ............... 600/437 |
| 6,530,885 | B1 * | 3/2003 | Entrekin et al. ............. 600/437 |
| 6,780,152 | B2 * | 8/2004 | Ustuner et al. ............... 600/443 |

(Continued)

FOREIGN PATENT DOCUMENTS

| JP | 10-136196 | 5/1998 |
| JP | 2003-319165 | 11/2003 |

(Continued)

OTHER PUBLICATIONS

Josien P. W. Pluim et al., "Mutual-Information-Based Registration of Medical Images: A Survey", IEEE Transactions on Medical Imaging, vol. 22, No. 8, Aug. 2003, pp. 986-1004.

(Continued)

*Primary Examiner* — Tse Chen
*Assistant Examiner* — Bradley Impink
(74) *Attorney, Agent, or Firm* — Oblon, Spivak, McClelland, Maier & Neustadt, L.L.P.

(57) ABSTRACT

An ultrasonic diagnostic apparatus is configured as follows. Namely, an ultrasonic diagnostic apparatus is provided with a control unit which collets a heart synchronized signal, etc. synchronizing with workings of a heart of a patient, etc., and an image processing unit which detects an overlapped area of the three-dimensional data acquired by ultrasonic scanning from different echo windows, for the three dimensional image data group acquired in the same time phase in synchronization with the heart synchronized signal or aspiration synchronized signal, combines the three-dimensional image data, and generates a panorama three-dimensional image data group consisting of panorama three-dimensional image data which are continued in time and have a display area larger than each of the three-dimensional image data.

12 Claims, 7 Drawing Sheets

(56) References Cited

U.S. PATENT DOCUMENTS

| | | | | |
|---|---|---|---|---|
| 6,980,844 | B2* | 12/2005 | Schoisswohl | 600/407 |
| 7,033,320 | B2* | 4/2006 | Von Behren et al. | 600/443 |
| 7,450,746 | B2* | 11/2008 | Yang et al. | 382/131 |
| 7,828,731 | B2* | 11/2010 | Baba et al. | 600/437 |
| 2002/0167533 | A1* | 11/2002 | Tirumalai et al. | 345/629 |
| 2006/0025669 | A1 | 2/2006 | Ramamurthy et al. | |
| 2007/0167801 | A1 | 7/2007 | Webler et al. | |

FOREIGN PATENT DOCUMENTS

| | | |
|---|---|---|
| JP | 2006-122657 | 5/2006 |
| JP | 2007-109166 | 4/2007 |
| JP | 2007-244746 | 9/2007 |

OTHER PUBLICATIONS

Office Action mailed Jan. 22, 2013 in Japanese Application No. 2008-021854 filed Jan. 31, 2008 (w/English translation).

* cited by examiner

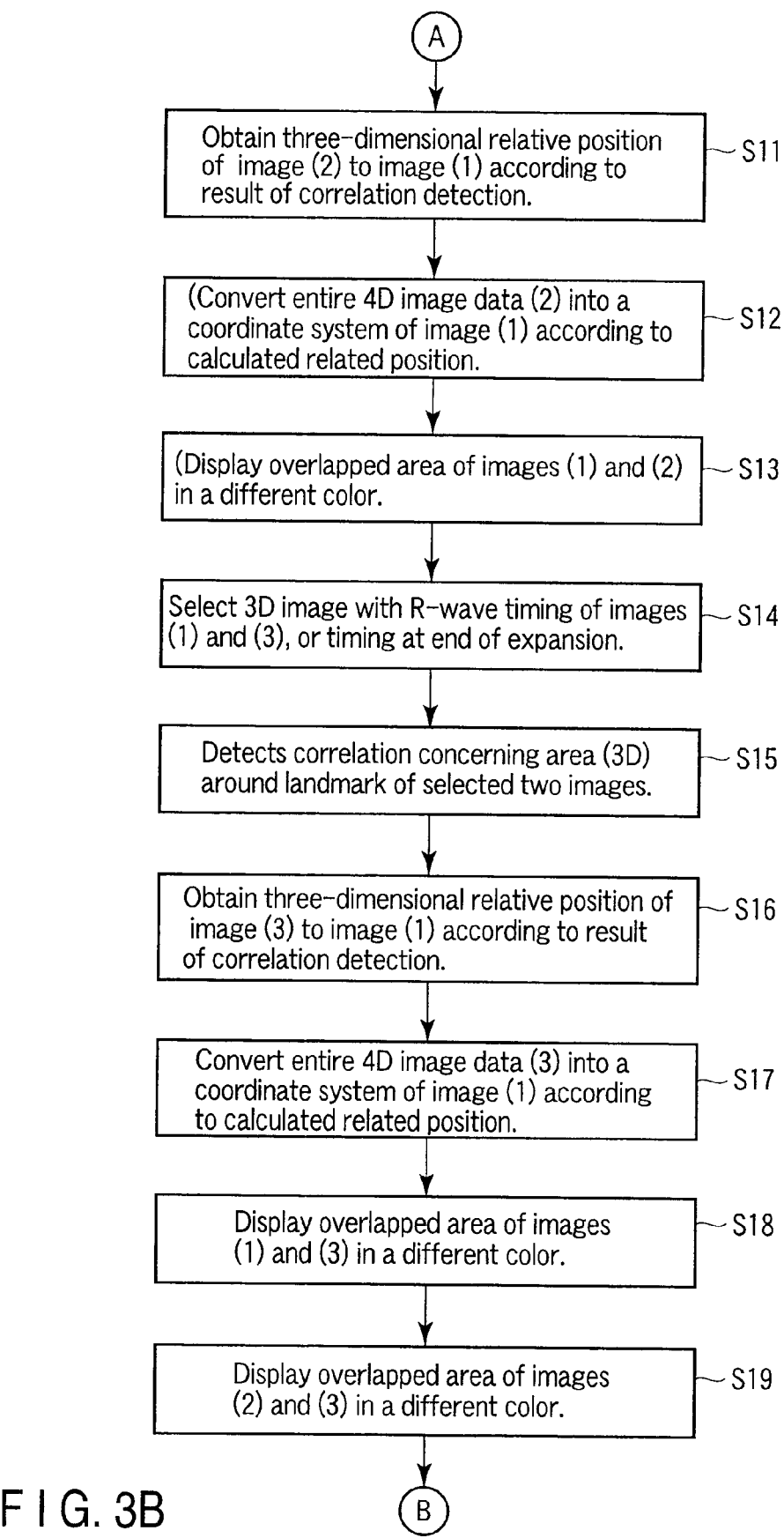
F I G. 3B

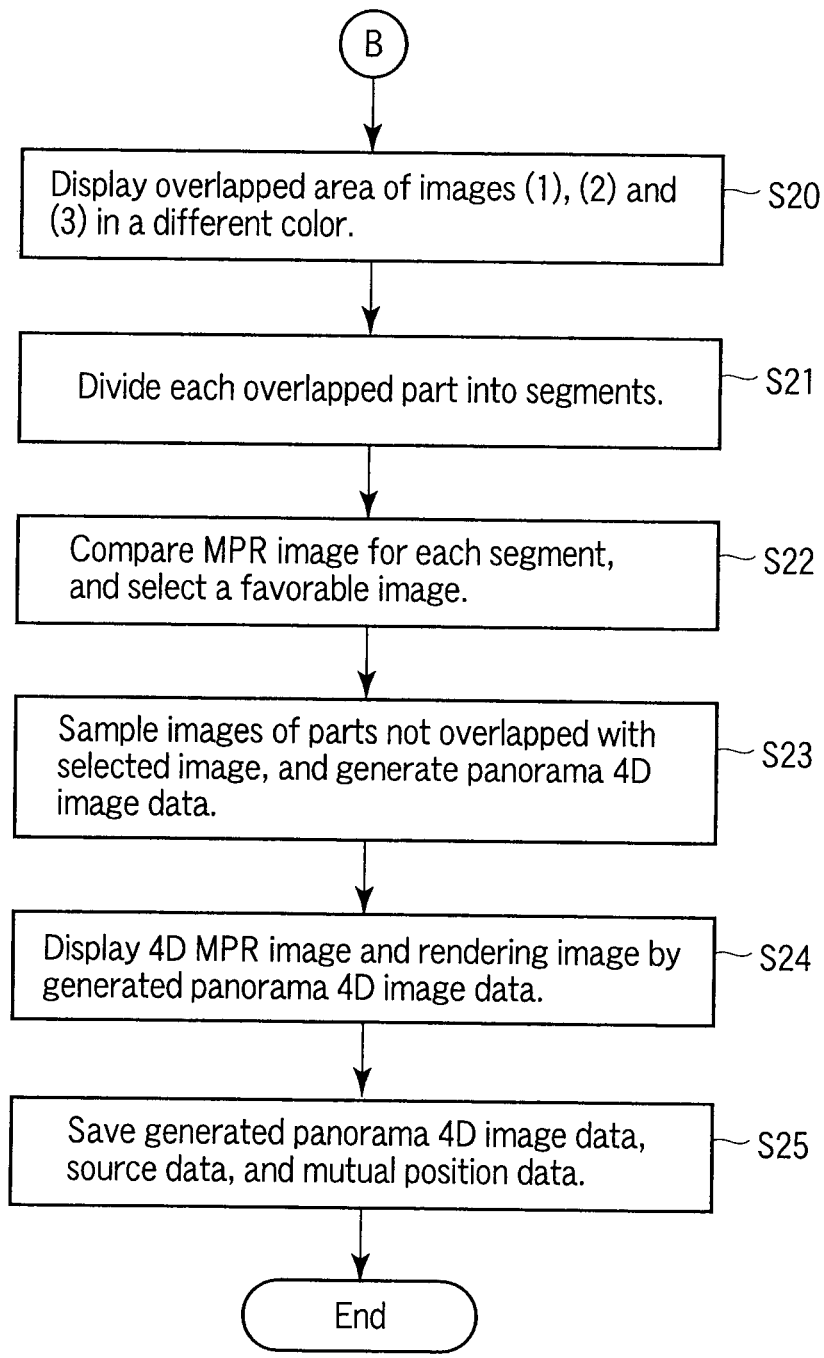
F I G. 3C

ULTRASONIC DIAGNOSTIC APPARATUS, DIAGNOSTIC IMAGING APPARATUS, AND PROGRAM

CROSS-REFERENCE TO RELATED APPLICATIONS

This application is based upon and claims the benefit of priority from prior Japanese Patent Application No. 2008-021854, filed Jan. 31, 2008, the entire contents of which are incorporated herein by reference.

BACKGROUND OF THE INVENTION

1. Field of the Invention

The present invention relates to an ultrasonic diagnostic apparatus, a diagnostic imaging apparatus, and a program for diagnosis by imaging internal organs of a patient. In particular, the present invention relates to an ultrasonic diagnostic apparatus, a diagnostic imaging apparatus, and a program, which form three-dimensional images of internal organs of a patient, and display the three-dimensional images by using ultrasonic waves.

2. Description of the Related Art

An ultrasonic diagnostic apparatus enables real-time observation of sectional images of a patient. In recent years, an ultrasonic diagnostic apparatus capable of acquiring and displaying three-dimensional image data at high speed has been rapidly developed. An ultrasonic diagnostic apparatus capable of acquiring and displaying three-dimensional sectional images and dynamic images consisting of three-dimensional sectional images has been provided.

For diagnosis of a heart and an area close to a heart, it is necessary to obtain real-time sectional images with sufficient time resolution, because a heart works fast. Therefore, an ultrasonic diagnostic apparatus is indispensable for diagnosis of a heart and an area close to a heart, and its importance has been increased in recent years.

However, an ultrasonic diagnostic apparatus has following problems. For example, comparing with large diagnostic imaging apparatus, such as a CT scanner and MRI apparatus, an observable range is narrow. For an ultrasonic diagnostic apparatus, it is difficult to observe a wide area including a concerned area, for example, a whole organ such as a heart.

Further, in a heart and an area close to a heart, there are obstacles hard to transmit ultrasonic waves. Therefore, when a heart is observed by an ultrasonic diagnostic apparatus, an echo window observable by using ultrasonic waves is limited by the lungs and ribs surrounding the heart, and it is very difficult to observe the whole heart from an echo window at one location.

Namely, an ultrasonic diagnostic apparatus is difficult to acquire and display sectional diagnostic images clearly showing a whole heart of a patient. Therefore, under the present circumstances, when inspecting a heart, an inspector selects a most suitable echo window from those of each part of a heart, or according to variations among individuals. Such ultrasonic inspection of a heart requires various inspection techniques, and much time is required to master the techniques. The ultrasonic inspection itself requires long time.

In recent years, even a large diagnostic imaging apparatus such as a CT scanner and a MRI apparatus can acquire and display three-dimensional diagnostic images of a heart in detail by using sectional diagnostic images acquired in synchronization with an electrocardiogram. Therefore, it is possible to diagnose a heart by comparing the sectional images of a heat obtained by an ultrasonic diagnostic apparatus and various modality apparatus such as a CT scanner and a MRI apparatus.

However, when three-dimensional images of a heart obtained by an ultrasonic diagnostic apparatus and a CT scanner, for example, a acquirable/displayable area is limited in a three-dimensional image obtained by an ultrasonic diagnostic apparatus, and it is difficult to find an image showing the same area as that in a three-dimensional image obtained by a CT scanner. Further, even when three-dimensional images obtained by an ultrasonic diagnostic apparatus are displayed side by side, each display area is limited, and it is difficult to compare the images.

In the above circumstances, the following technique has been proposed in Jpn. Pat. Appln. KOKAI Publication No. 2006-122657, for example. The Jpn. Pat. Appln. KOKAI Publication No. 2006-122657 discloses an ultrasonic diagnostic apparatus, which includes an array oscillator comprising oscillation elements arranged like a concaved cylinder, and a transmission/reception means connected to the array oscillator, wherein the oscillation elements consist of lines of oscillation elements aligned along the axis of the cylinder, each line of the oscillation elements consist of lines of oscillation elements aligned along the circumference of the cylinder, the transmission/reception means executes first electronic scanning along the axis of the cylinder, as electronic sector scanning or electronic linear scanning, and executes second electronic scanning along the circumference of the cylinder, as electronic linear scanning. The ultrasonic diagnostic apparatus disclosed in the Jpn. Pat. Appln. KOKAI Publication No. 2006-122657 can transmit and receive ultrasonic waves through a clearance in a structure in a living body.

However, according to the technique disclosed in the Jpn. Pat. Appln. KOKAI Publication No. 2006-122657, though a two-dimensional array probe improved to have a shape easy to insert into a clearance between ribs of a patient, the specialized shape makes it difficult to manufacture the probe itself. Further, the technique disclosed in the Jpn. Pat. Appln. KOKAI Publication No. 2006-122657 is not a technique to enable improvement of picture quality by an ultrasonic wave radiation angle or depth, and does not absolutely solve the above problem.

BRIEF SUMMARY OF THE INVENTION

The invention has been made in the above circumstances. Accordingly, it is an object of the invention to provide an ultrasonic diagnostic apparatus, a diagnostic imaging apparatus, and a program, which are configured to acquire and display three-dimensional images showing clearly a whole organ at high speed without limiting an echo window, even in an area including a fast-working organ like a heart, in the organ or in an area close to the organ.

In order to achieve the above object, according to a first aspect of the invention, there is provided an ultrasonic diagnostic apparatus, which executes ultrasonic scanning of the same area in a patient twice or more times from different echo windows, so as to overlap at least one part, and acquires three-dimensional image data group consisting of three-dimensional image data continued in time by the ultrasonic scanning from different echo windows, comprising an image data acquisition unit for acquiring the three-dimensional image data group on the patient; a living body signal acquisition unit which acquires at least one of a heart synchronized signal synchronizing with workings of a heart of the patient and an aspiration synchronized signal synchronizing with aspiration of the patient, when the image data acquisition unit acquires the three-dimensional image data group on the patient; and an image processing unit which detects an overlapped area of the three-dimensional data acquired by the ultrasonic scanning from different echo windows, for the three dimensional image data group acquired in the same time phase in synchronization with the heart synchronized signal or aspiration synchronized signal, combines the three-dimensional image data acquired by the ultrasonic scanning from different echo windows, based on the overlapped area, and generates a panorama three-dimensional image data group consisting of panorama three-dimensional image data which are continued in time and have a display area larger than each of the three-dimensional image data.

In order to achieve the above object, according to a second aspect of the invention, there is provided a diagnostic imaging apparatus, which executes scanning of the same area in a patient twice or more times from different echo windows, so as to overlap at least one part, and acquires three-dimensional image data group consisting of three-dimensional image data continued in time by the scanning from different echo windows, comprising an image data acquisition unit for acquiring the three-dimensional image data group on the patient; a living body signal acquisition unit which acquires at least one of a heart synchronized signal synchronizing with workings of a heart of the patient and an aspiration synchronized signal synchronizing with aspiration of the patient, when the image data acquisition unit acquires the three-dimensional image data group on the patient; and an image processing unit which detects an overlapped area of the three-dimensional data acquired by the scanning from different echo windows, for the three dimensional image data group acquired in the same time phase in synchronization with the heart synchronized signal or aspiration synchronized signal, combines the three-dimensional image data acquired by the ultrasonic scanning from different echo windows, based on the overlapped area, and generates a panorama three-dimensional image data group consisting of panorama three-dimensional image data which are continued in time and have a display area larger than each of the three-dimensional image data.

In order to achieve the above object, according to a third aspect of the invention, there is provided a program which operates a computer as an ultrasonic diagnostic apparatus, which executes ultrasonic scanning of the same area in a patient twice or more times from different echo windows, so as to overlap at least one part, and acquires three-dimensional image data group consisting of three-dimensional image data continued in time by the ultrasonic scanning from different echo windows, and causes a computer to realize an image data acquisition function for acquiring the three-dimensional image data group on the patient; a living body signal acquisition function which acquires at least one of a heart synchronized signal synchronizing with workings of a heart of the patient and an aspiration synchronized signal synchronizing with aspiration of the patient, when the three-dimensional image data group on the patient is acquired by the image data acquisition function; and an image processing function which detects an overlapped area of the three-dimensional data acquired by the ultrasonic scanning from different echo windows, for the three dimensional image data group acquired in the same time phase in synchronization with the heart synchronized signal or aspiration synchronized signal, combines the three-dimensional image data acquired by the ultrasonic scanning from different echo windows, based on the overlapped area, and generates a panorama three-dimensional image data group consisting of panorama three-dimensional image data which are continued in time and have a display area larger than each of the three-dimensional image data.

According to the invention, there is provided an ultrasonic diagnostic apparatus, a diagnostic imaging apparatus, and a program, which are configured to acquire and display three-dimensional images showing clearly a whole organ at high speed without limiting an echo window, even in an area including a fast-working organ like a heart, in the organ or in an area close to the organ.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3B is a second part of a flowchart of a process of combining four-dimensional image data;

FIG. 3C is a third part of a flowchart of a process of combining four-dimensional image data;

DETAILED DESCRIPTION OF THE INVENTION

An embodiment of the invention will be explained hereinafter with reference to the accompanying drawings.

Figure 1:
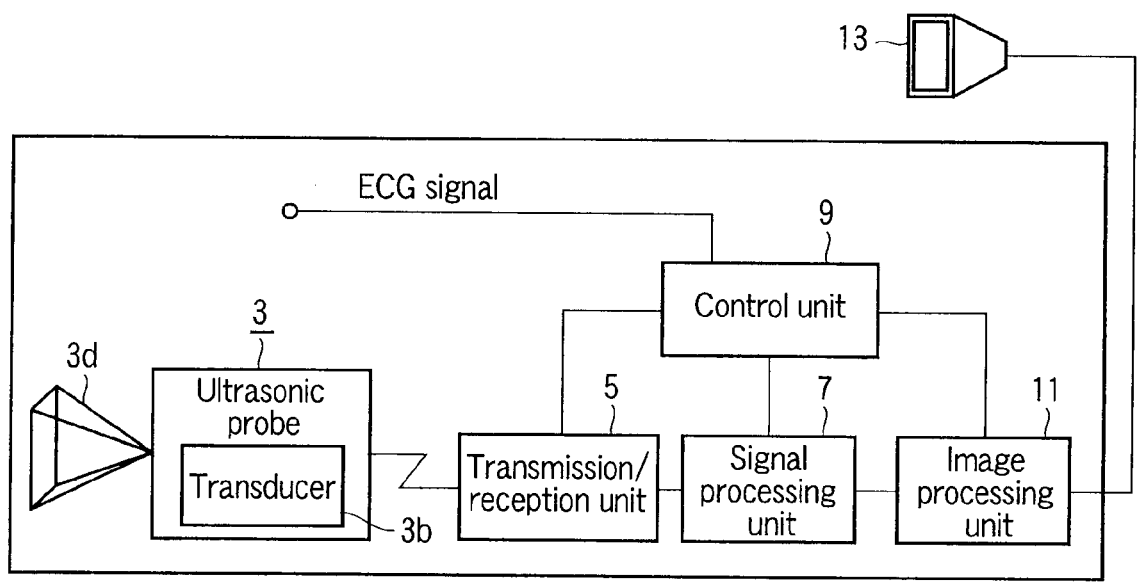
FIG. 1 is a diagram showing an example of configuration of an ultrasonic diagnostic apparatus according to an embodiment of the invention.

FIG. 1 is a diagram showing an example of configuration of an ultrasonic diagnostic apparatus according to this embodiment. As shown in the drawing, an ultrasonic diagnostic apparatus 1 comprises an ultrasonic probe 3, a transmission/reception unit 5, a signal processing unit 7, a control unit 9, and an image processing unit 11. Image data output from the image processing unit 11 is displayed on a display 13.

Figure 2:
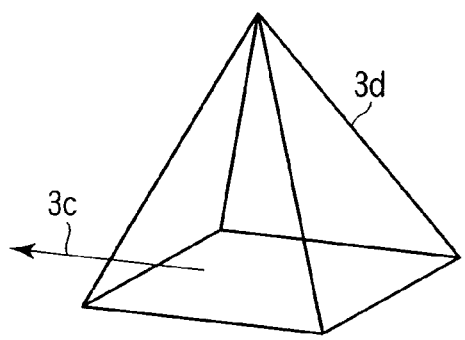
FIG. 2 is a diagram showing an ultrasonic probe.

The ultrasonic probe 3 has a transducer 3b for transmitting and receiving ultrasonic waves. For example, as shown in FIG. 2, a two-dimensional scanning line from the ultrasonic probe 3 is moved in the direction of the arrow 3c, thereby forming a three-dimensional scanning space area 3d.

The transmission/reception unit 5 includes a transmission circuit, a receiving circuit, and an analog-to-digital conversion circuit.

The transmission circuit generates drive signals to be applied to the transducer 3b, and applies a delay time to each drive signal, based on a transmission delay pattern selected by the control unit 9. The transmission circuit may be configured to adjust to supply the drive signals to the ultrasonic probe 3 by adjusting a delay amount, so that an ultrasonic wave transmitted from the ultrasonic probe 3 forms an ultrasonic beam. The transmission circuit may also be configured to supply the drive signals to the ultrasonic probe 3, so that ultrasonic waves transmitted from the ultrasonic probe 3 at a time reach an entire imaging area of a patient.

The receiving circuit amplifies detection signals output from the ultrasonic probe 3, applies a delay time to the detection signals based on a reception delay pattern selected by the control unit 9, and adds the detection signals, thereby adjusting a receiving focus. This receiving focus adjustment forms a radio frequency signal (a RF signal), in which a focus of ultrasonic wave is adjusted.

The analog-to-digital conversion circuit converts an analog RF signal to a digital RF signal (RF data).

The signal processing unit 7 corrects attenuation of the RF data by a distance depending on the depth of an ultrasonic wave reflecting position, by sensitivity time gain control (STC), and generates image data by detecting an envelope.

The control unit 9 inclusively controls the whole ultrasonic diagnostic apparatus 1. As shown in FIG. 1, the control unit 9 receives an electrocardiogram (ECG) signal to be measured in a heart.

The image processing unit 11 executes image processing for image data output from the signal processing unit 7, and outputs a resultant image data to the display 13. This processing by the image processing unit 11 is one of main features of the ultrasonic diagnostic apparatus according to this embodiment, and will be described later in detail.

As explained above, in the ultrasonic diagnostic apparatus 1 according to this embodiment, three-dimensional ultrasonic image data (hereinafter, called 3D image data) is acquired by high-speed three-dimensional scanning of ultrasonic waves by the ultrasonic probe 3, and processing by the transmission/reception unit 5 and signal processing unit 7.

Hereinafter, an explanation will be given of the outline of a process of generating synthetic panorama four-dimensional data (described later in detail) that is one of main features of the ultrasonic diagnostic apparatus according to this embodiment, to facilitate the understanding of the features of the ultrasonic diagnostic apparatus according to this embodiment.

First, an ECG signal is also acquired when 3D image data is acquired, as described. Then, the 3D image data acquired at high speed is applied to the image processing unit 11, together with the ECG signal, as 3D image data continued in time (hereinafter, called 4D image data for convenience), and is subjected to image processing in the image processing unit 11 as described later.

The 4D image data is acquired from at least two or more different echo windows in an overlapped area in a scanning range.

For the 3D image data constituting the 4D image data acquired from the different echo windows, position searching is done by correlating the images in this embodiment, in order to align the relative positions of the overlapped area. This makes it possible to find a relatively aligned area in the overlapped area in the 3D image data, and to adjust the position so that they are overlapped, thereby determining a combining position.

Further, the overlapped area of the 4D image data is divided into segments. For each of the divided segments, image data acquired from which echo window is the most suitable is determined, and the most suitable image data is selected.

By using the selected image data, positioning is done for the overlapped area of the 3D image data acquired from the different echo windows in the same time phase of the signal synchronizing with the working of a heart or aspiration, and the resultant data is synthesized (combined), thereby forming combined panorama 4D image data consisting of panorama three-dimensional image data, which are continued in time and have a display area larger than the above three-dimensional image data.

Further, by using the mutual position information that is the information about the above positioning of the overlapped area, 3D data is combined for all other time phases (heartbeat synchronized time phase, and aspiration synchronized time phase).

A predetermined landmark is set when the 4D image data is acquired, and the landmark is used for the position searching by correlating the images.

When the 3D image data (4D image data) acquired from the different echo windows are combined, the overlapped area and other areas are displayed in different colors on the display 13 in order to clarify the overlapped area.

Figure 3A:
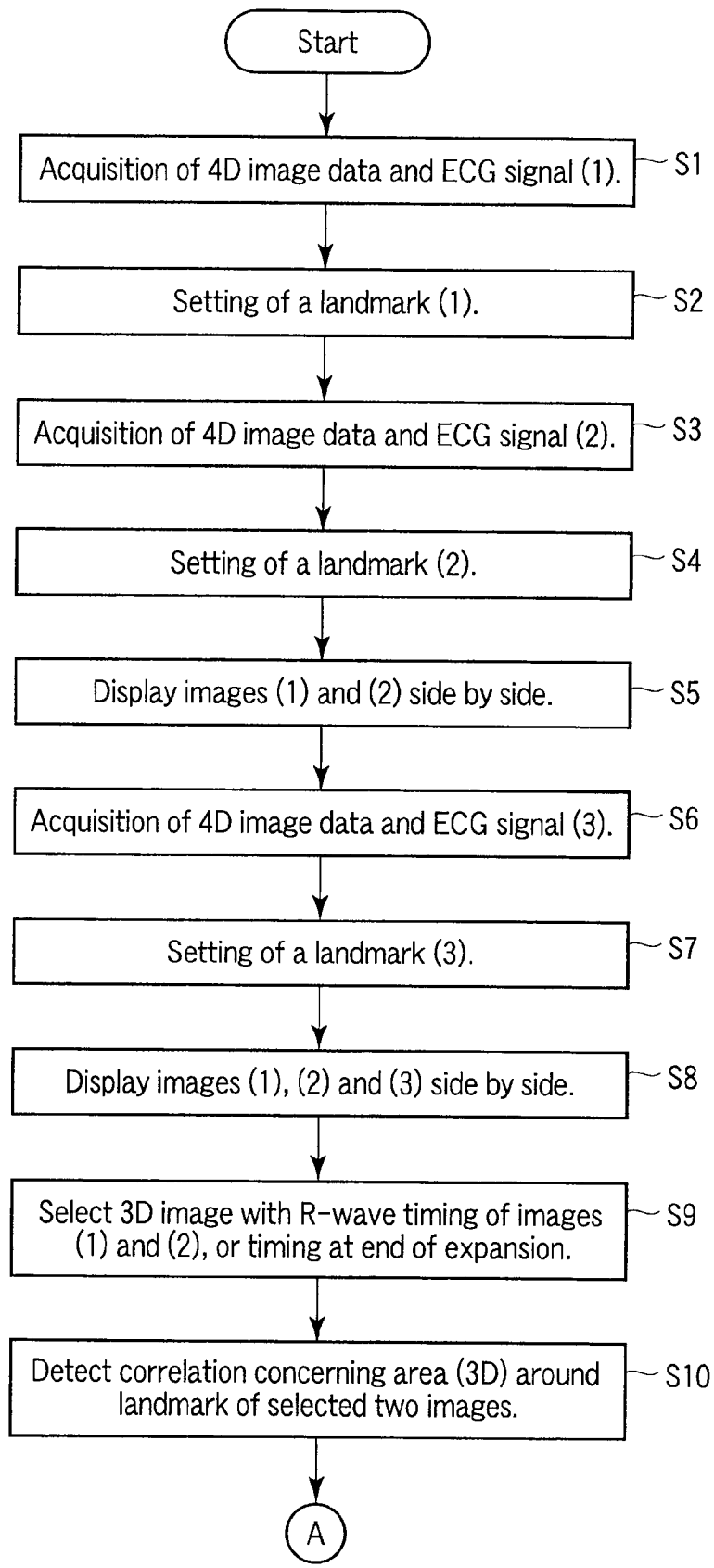
FIG. 3A is a first part of a flowchart of a process of combining four-dimensional image data.
Figure 4:
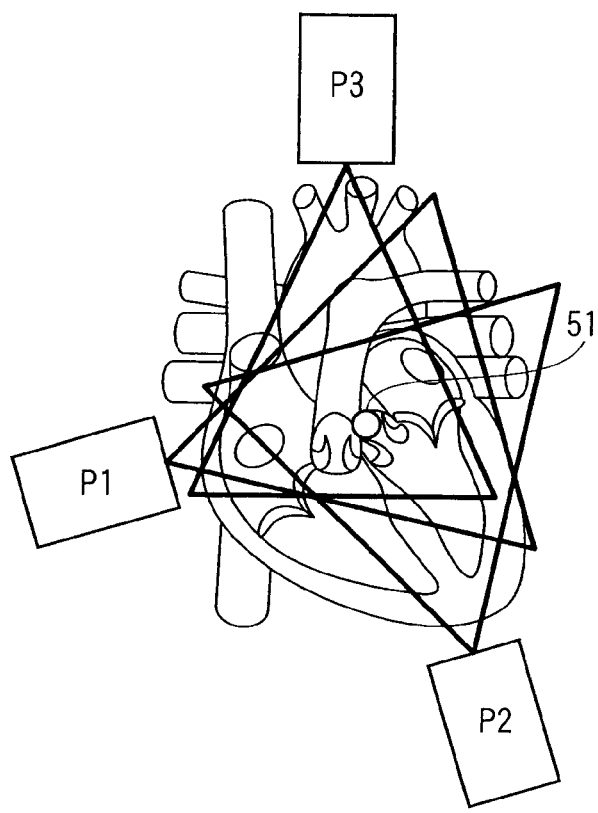
FIG. 4 is a perspective view showing parts of a heart.

Hereinafter, a detailed explanation will be given of a process of combining the combined panorama 4D image data by the control unit 9 and image processing unit 11, with reference to the flowcharts shown in FIGS. 3A to 3C. FIG. 4C is a perspective view showing parts of a heart.

Figure 5:
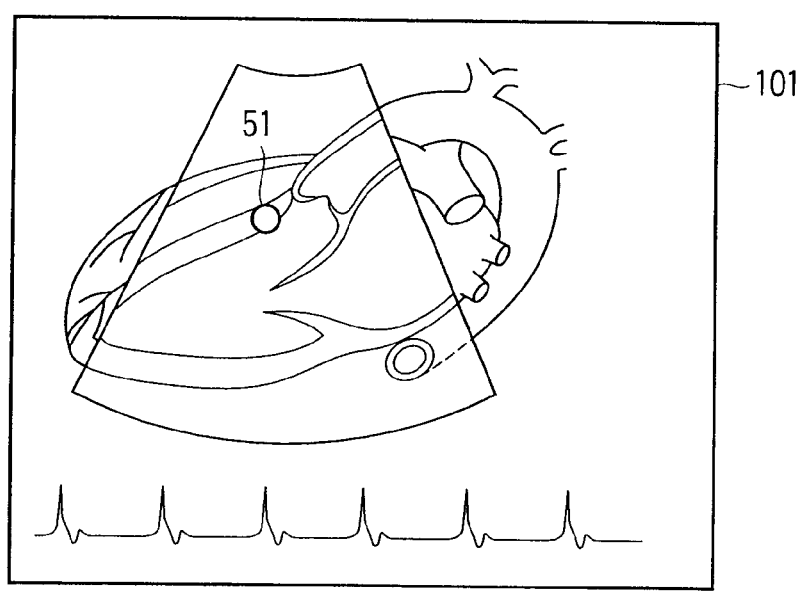
FIG. 5 is a diagram showing an example of four-dimensional image data acquired by three-dimensional scanning from an echo window of a bone near a sternum.
Figure 6:
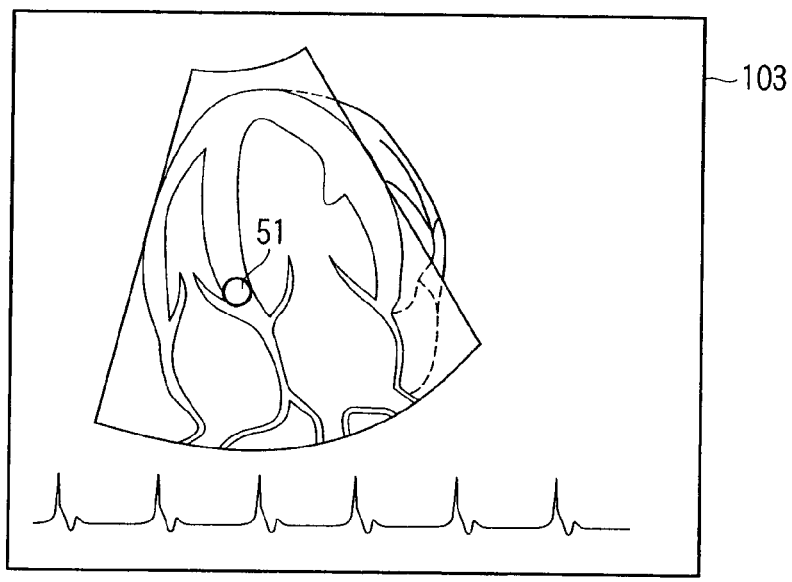
FIG. 6 is a diagram showing an example of four-dimensional image data acquired by three-dimensional scanning from an echo window of a peak of a heat.

In each step explained hereinafter, before execution of image acquisition in a three-dimensional panoramic mode, an acquisition area is confirmed in a two-dimensional mode. When image acquisition is executed by three-dimensional scanning in a three-dimensional panoramic mode, a display screen in the display 13 is a display screen for acquisition of 3D images. A layout of this display screen may be a layout of a display screen including a 3D main sectional MPR image to be acquired (refer to FIGS. 5 and 6).

First, 4D image data and ECG signal are acquired (step S1). Specifically, the following operation is performed in this step S1.

In step S1, 4D image data 101 (refer to FIG. 5) is acquired by making three-dimensional scanning from an echo window of a bone close to a sternum (from the echo window indicated by a reference number P1 in FIG. 4) by using the ultrasonic probe 3, and at the same time, ECG signal waveform data is acquired. Namely, 4D image data and ECG signal waveform data are acquired.

Figure 7:
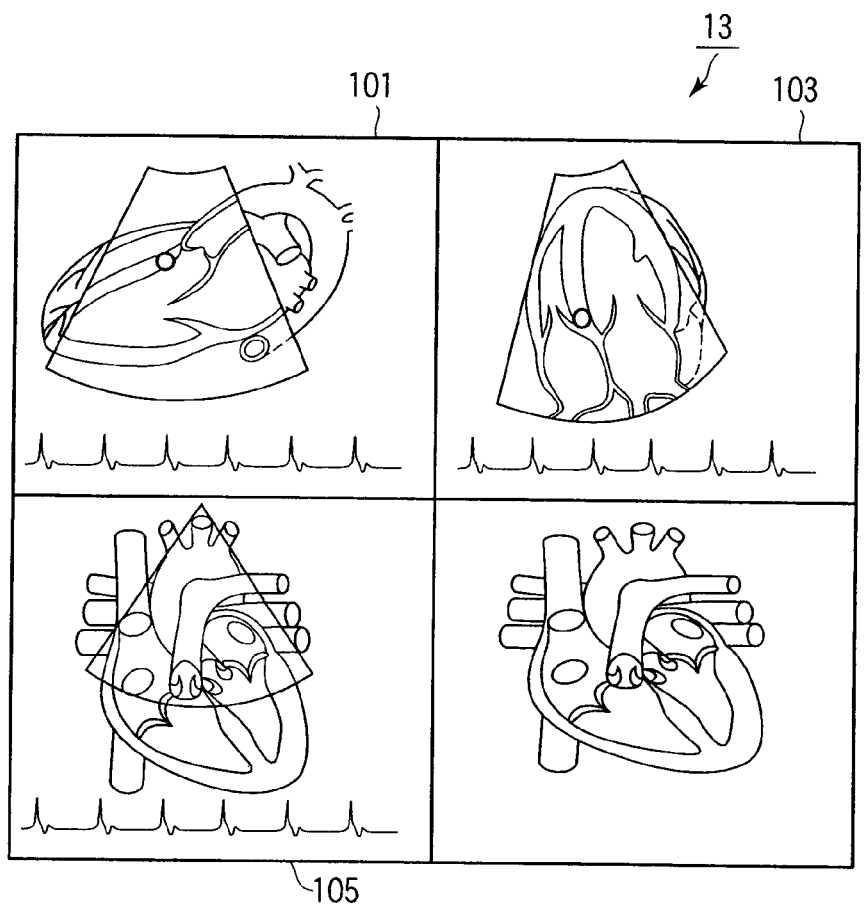
FIG. 7 is a diagram showing an example of layout of a display screen at the time of acquiring four-dimensional image data.

The acquired 4D image data 101 is once displayed on the display 13 as one of the screens (4 screens) shown in FIG. 7.

After the operation in step S1, a landmark 51 is set as a point for searching image correlation for combining between the obtained 4D image data (step S2).

Then, the ultrasonic probe 3 is moved, and three-dimensional scanning is made from a peak of a heart (from an echo window indicated by a reference number P2 in FIG. 4), and 4D image data 103 (refer to FIG. 6) and ECG signal waveform data are acquired (step S3).

After the operation in step S3, a landmark 51 is set as a point for searching image correlation between the obtained 4D image data (step S4).

The acquired 4D image data 103 is once displayed on the display 13 as one of the screens shown in FIG. 7 (4 screens in the example shown in FIG. 7), like the 4D image 101 obtained in step S1, in a layout adjacent to the 4D image data 101 obtained in step S1 (step S5).

Further, the ultrasonic probe 3 is moved, three-dimensional scanning is made from a base of a heart (from an echo window indicated by a reference number P3 in FIG. 4), and 4D image data 105 (refer to FIG. 7) and ECG signal waveform data are acquired (step S6).

After the operation in step S6, a landmark is set as a point for searching image correlation for combining between the obtained 4D image data (step S7).

Then, the image correlation is detected as follows in the area around the landmark 51.

First, though not shown in the drawings, the 4D image data obtained in steps S1, S3 and S6 are displayed on the display 13 in a layout in which they are arranged side by side (step S8).

The 3D image data (MPR image), which constitutes one of the 4D image data 101 and 103 (here, the 4D image data 101), is set in a form including the landmark 51. 3D image data, which is in the same time phase and most similar to the above-set 3D image data and a R-wave of an ECG signal, is searched from the 3D image data constituting the other 4D image data (here, the 4D image data 103), by detecting correlation to an area close to the landmark 51 (step S9 and step S10).

In the above example, the searching is attempted for the 3D image data, which is in the same time phase to the above-set 3D image data and R-wave of ECG signal. The searching may also be made for the other 3D image data at the timing of the end of expansion, for example.

As a concrete method of detecting correlation, a method of detecting correlation between images, which is called a maximum entropy method, can be said an effective method. This maximum entropy method detects correlation by searching a most similar area in a three-dimensional space.

It is also possible to make positioning with higher accuracy is also possible by pattern matching in all time phases, or in two or more time phases in one heartbeat.

When the 3D image data which are most correlated are detected in steps S9 and S10, a relative position between the 4D image data is calculated by overlapping two detected 3D image data (step S11).

Figure 8:
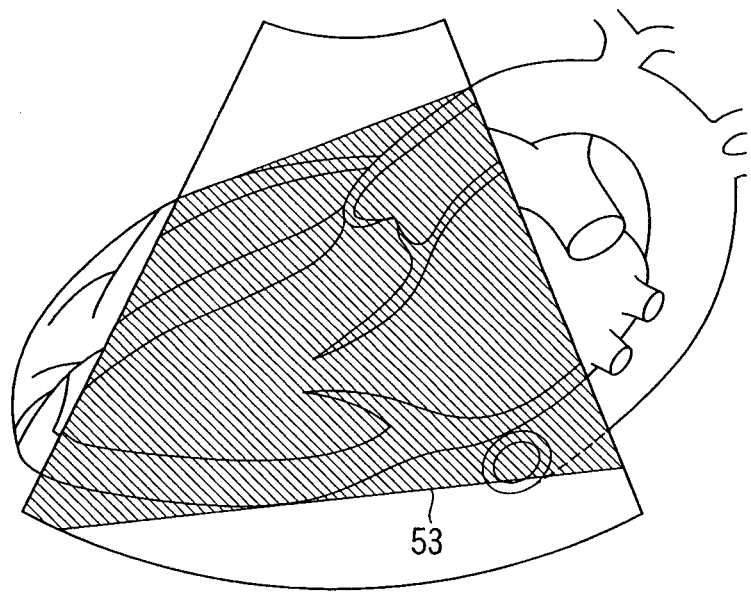
FIG. 8 is a diagram showing an example of displaying an overlapped area of four-dimensional image data acquired from different echo windows, in a different color from the other parts.

Then, the entire 4D image data 103 is converted to the coordinates of the 4D image data 101, based on the relative position calculated in step S11 (step S12). Further, the overlapped area of the 4D image data 101 and 103 (hereinafter, called an overlapped area) is displayed in a different color from the other areas, as shown in FIG. 8, for example (the overlapped area 53 is shown by hatching in FIG. 8) (step S13).

Figure 9:
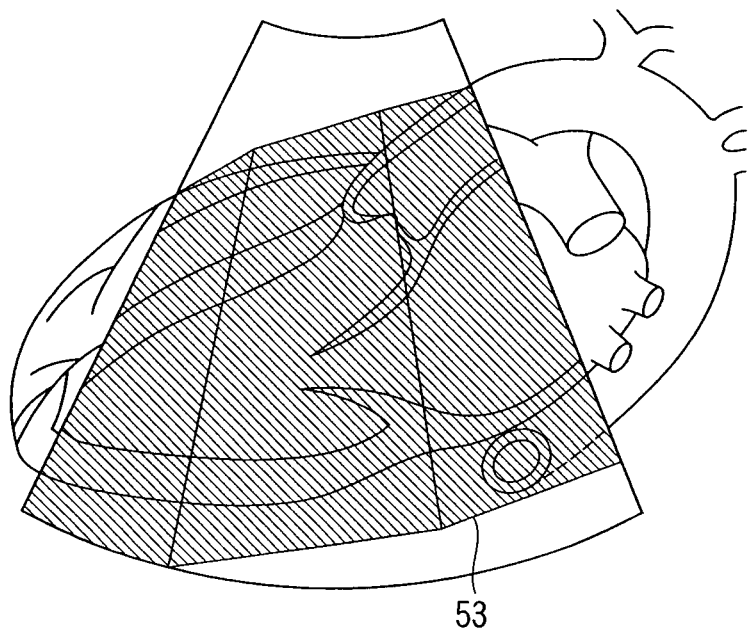
FIG. 9 is a diagram showing an example of displaying an overlapped area of four-dimensional image data acquired from different echo windows, in a different color from the other parts.

The 4D image data 101 and 4D image data 105 acquired in step S6 are subjected to the same processing as in steps S9 to S13 (step S14 to step S18), and the overlapped area of the 4D image data 101 and the 4D image data acquired in step S6 is displayed in a different color from the other areas, as shown in FIG. 9, for example (the overlapped area 53 is shown by hatching in FIG. 9).

Similarly, the overlapped area of the 4D image data 103 and the 4D image data 105 acquired in step S6 is displayed in a different color from the other areas (step S19). The overlapped area of the 4D image data 101, 4D image data 103, and 4D image data 105 acquired in step S6 is displayed in a different color from the other areas (step S20).

Images may be interpolated in each overlapped area and in a boundary area between the overlapped area and its outside area, by filtering with a Gauss filter or a median filter, for example.

Four-dimensional image data is acquired from different echo windows in the above steps, an overlapped area of these 4D image data is detected, and the overlapped area is divided into segments (step S21).

Specifically, in step S21, a user divides an overlapped area by setting a division line on a MPR image, for example. Images may be interpolated in a boundary area between the segments, by filtering with a Gauss filter or a median filter, for example.

For each segment divided in step S21, image data acquired from which echo window is the most suitable for the binding operation described later is determined, and the most suitable image data is selected (step S22). Namely, in this embodiment, image data is not selected as a choice between two, and a most suitable image data is selected as follows.

There are two methods of selecting image data in step S22.

In a first method, a user selects candidate image data by viewing a MPR image. In this case, it is effective to display image data by arranging on one screen of the display 13. It is of course permitted to generate/reproduce and compare 4D image data as an image after synthesizing (combining). It is also available to convert the frequency of the candidate image data, and to select a high-frequency component based on the result of conversion.

There is the following concrete method. The candidate image data are compared in a specific part of a high-frequency area of a histogram of the frequency of pixel brightness against the number of gray levels in the image related to these image data, and the image data, which includes more frequency components corresponding to the specific part of the high-frequency area, is selected.

The specific part in the high-frequency area depends on the image setting in an apparatus to be used or the characteristics of a probe to be used, and cannot be uniquely defined. However, the specific part of the high-frequency area can be suitably set for each apparatus having the same setting. More specifically, an area corresponding to a frequency component close to a frequency higher than a center frequency of a histogram of each image data is set as a specific part of the high-frequency area.

It is also available to compare the center frequencies in a histogram of candidate image data, and to select image data whose center frequency is higher.

A second method uses an autofocus technique. The above method of comparing high-frequency components is one of the autofocus techniques. In this method, the control unit 9 and image processing unit 11 can execute the above selection, and a user can automatically select most suitable image data by doing nothing about the above selection.

In case of observing a large fast-working organ such as a heart, it is difficult to obtain clear image data, compared with a case of observing other human parts. Further, in case of 3D image data, resolution tends to be high in the depth direction, but low in the dimensional direction. Thus, even in case of observing the same human part, a picture quality may be extremely different depending on an echo window used to acquire image data.

In the above circumstances, in this embodiment, more favorable image data is selected as image data related to synthesizing (combining), by making the operation in step S22. By this operation, the whole field of view is enlarged, and the picture quality is greatly improved.

After the operation in step S22, the selected image data is synthesized (combined), and synthetic panorama 4D image data is generated (step S23). Specifically, when 4D image data acquired from each echo window is expressed in voxels, for example, synthetic panorama 4D image data is generated by re-sampling each voxel converted to coordinates in step S17, to a voxel of the same coordinates including all.

The synthetic panorama 4D image data generated in step S23 is displayed on the display 13 as a MPR image or a rendering image, for example (step S24). Further, the synthetic panorama 4D image data generated in step S23 is stored in a storage means (not shown) (step S25). In this case, the image data used as a base of the synthetic panorama 4D image data and mutual position data indicating the overlapped areas of them may of course be stored in the storage means (not shown) together with the synthetic panorama 4D image data.

A series of the above image processing by the control unit 9 and image processing unit 11 can be programmed. The programmed processing can be stored in a storage medium. Such a program can be easily sold and distributed as a software product independent of the ultrasonic diagnostic apparatus 1. It is also possible to use the technique related to this embodiment on the other hardware.

As explained herein, according to this embodiment, it is possible to provide an ultrasonic diagnostic apparatus, a diagnostic imaging apparatus, and a program, which are configured to acquire and display three-dimensional images showing clearly a whole organ such as a heart at high speed without limiting an echo window, in the organ or nearby areas, even in an area including a fast-working organ like a heart, in the organ or in an area close to the organ.

Specifically, according to this embodiment, 3D (4D) image data can be generated by combining 3D (4D) image data, even in an area in which an echo window for acquiring image data about a heart or parts around a heart is limited.

Besides, according to this embodiment, synthetic panorama 4D image data can be generated by simple processing, by combining 3D image data with 3D image data in other all time phases (heartbeat time phase, aspiration synchronized time phase), by using mutual position information used for positioning of the overlapped area in at least one or more areas.

Further, 3D image data can be easily combined at low cost, by the position searching by correlating the images for the 3D image data acquired from different echo windows, as a means for adjusting the relative positions in the overlapped area. The positioning can be made easily at high speed by using a landmark, as described above. A positioning method using a landmark is correct. There is another positioning method without using a landmark, such as pattern matching, in which forms are automatically recognized.

Further, according to this embodiment, after the relative positions of the overlapped area are adjusted for the 3D image data acquired from different echo windows, the overlapped area and other areas are displayed in different colors, and the user can easily recognize the overlapped area.

Further, an image selection function (step S22) is provided in this embodiment. This enables the user to easily select a favorable image, and to generate an entirely clear combined image (synthetic panorama 4D image data).

The overlapped area can be divided into segments, and an image is selected for each segment. This enables generation of an entirely clear combined image (synthetic panorama 4D image data).

By the filtering operation, the continuity in each boundary area is improved.

An embodiment of the invention has been explained herein. The invention is not limited to the embodiment described herein. The invention may be modified or applied without departing from the spirit and essential characteristics of the invention.

For example, a position sensor may be provided in the ultrasonic probe 3 in order to detect the overlapped area.

Further, the embodiment described herein includes various stages of the invention, and various embodiment of the invention can be extracted by appropriately combining the constituent elements disclosed herein. For example, the problem solved by the invention can be solved by eliminating some of the disclosed constituent elements. When the effect described in Effects of the Invention can be obtained, the configuration without using the eliminated constituent elements can be extracted as an embodiment of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus, comprising:
    a computer;
    a non-transitory computer readable medium storing program instructions which when executed by the computer results in performance of steps comprising,
    initiating ultrasonic scanning of the same region in a patient two or more times from different echo windows, so as to overlap at least one part,
    acquiring a three-dimensional image data group on the patient, the three-dimensional image data group consisting of three-dimensional image data continued in time by the ultrasonic scanning from the different echo windows,
    acquiring at least one of a heart synchronized signal synchronizing with workings of a heart of the patient and an aspiration synchronized signal synchronizing with aspiration of the patient, when the three-dimensional image data group on the patient is acquired,
    detecting an overlapped region of the three-dimensional data acquired by the ultrasonic scanning from different echo windows, for the three dimensional image data group acquired in the same time phase in synchronization with the heart synchronized signal or aspiration synchronized signal,
    combining the three-dimensional image data acquired by the ultrasonic scanning from different echo windows, based on the overlapped region,
    generating a panorama three-dimensional image data group consisting of panorama three-dimensional image data which are continued in time and have a display area larger than each of the three-dimensional image data,
    dividing the overlapped regions in three-dimensional image data, into segments;
    acquiring for each divided segment an average luminance of pixel values included in the image data of each echo window within said each divided segment, and
    selecting based on the average luminance acquired for each divided segment, the image data of only that echo window having a highest average luminance within each said divided segment to be used for the three-dimensional image data adopted for the combining operation.

2. The ultrasonic diagnostic apparatus according to claim 1, wherein the non-transitory computer readable medium stores further instructions which when executed by the computer causes execution of the following steps:
    detecting the overlapped region by searching the same overlapped region by an image correlation detection method, and adjusting the positions of the three-dimensional image data so that the same overlapped regions are overlapped;

converting coordinates of the three-dimensional image data, based on a result of the adjusting the positions; and performing the combining step by using the three-dimensional image data whose coordinates are converted by the converting step.

3. The ultrasonic diagnostic apparatus according to claim 2, wherein the combining step combines the three-dimensional image data acquired by the ultrasonic scanning from different echo windows in the same time phase in synchronization with the heart synchronized signal or aspiration synchronized signal, in one time phase, and then applies the information concerning the conversion of coordinates used in the combining step in said one time phase, to the combining step in another time phase.

4. The ultrasonic diagnostic apparatus according to claim 2, further comprising:

a display which displays three-dimensional image data coordinates converted in the converting step, and three-dimensional image data combined with the three-dimensional image data, in a state in which regions corresponding to the same part in the patient are overlapped;

wherein the non-transitory computer readable medium stores further instructions which when executed by the computer causes the display to display the regions corresponding to the same part, in the three-dimensional image data displayed by the display, in a different color from regions corresponding to other regions.

5. The ultrasonic diagnostic apparatus according to claim 2, wherein the non-transitory computer readable medium stores further instructions which when executed by the computer results in adding a landmark to a predetermined part in the three-dimensional image data and searching the same part by referring to the added landmark when acquiring the three-dimensional image data group.

6. The ultrasonic diagnostic apparatus according to claim 1, comprising an ultrasonic probe provided with a position sensor, and the detecting the overlapped region includes referring to the output of the position sensor.

7. The ultrasonic diagnostic apparatus according to claim 1, wherein the non-transitory computer readable medium stores further instructions which when executed by the computer results in filtering in a boundary region generated by the combining step, and in an region close to the boundary region.

8. The ultrasonic diagnostic apparatus according to claim 7, wherein the filtering comprises filtering with a Gauss filter.

9. The ultrasonic diagnostic apparatus according to claim 7, wherein the filtering comprises filtering with a median filter.

10. An ultrasonic diagnostic apparatus comprising:

a computer;

a non-transitory computer readable medium storing program instructions which when executed by the computer results in performance of steps comprising, initiating ultrasonic scanning of the same region in a patient two or more times from different echo windows, so as to overlap at least one part, acquiring a three-dimensional image data group on the patient, the three-dimensional image data group consisting of three-dimensional image data continued in time by the ultrasonic scanning from the different echo windows, acquiring at least one of a heart synchronized signal synchronizing with workings of a heart of the patient and an aspiration synchronized signal synchronizing with aspiration of the patient, when the three-dimensional image data group on the patient is acquired, detecting an overlapped region of the three-dimensional data acquired by the ultrasonic scanning from different echo windows, for the three dimensional image data group acquired in the same time phase in synchronization with the heart synchronized signal or aspiration synchronized signal, combining the three-dimensional image data acquired by the ultrasonic scanning from different echo windows, based on the overlapped region, generating a panorama three-dimensional image data group consisting of panorama three-dimensional image data which are continued in time and have a display area larger than each of the three-dimensional image data, dividing the overlapped regions in three-dimensional image data, into segments;

generating, for each echo window within each said divided segment, a histogram of the frequency of pixel brightness against the number of gray levels, comparing the histograms for each echo window within each said divided segment and selecting the three-dimensional image data, whose central frequency in the histogram is the highest, as the three-dimensional image data adopted in the combining step.

11. A non-transitory computer readable medium storing program instructions configured to operate a computer as an ultrasonic diagnostic apparatus, and to cause the computer to perform steps comprising:

initiating ultrasonic scanning of the same region in a patient two or more times from different echo windows, so as to overlap at least one part;

acquiring a three-dimensional image data group on the patient, the three-dimensional image data group consisting of three-dimensional image data continued in time by the ultrasonic scanning from the different echo windows;

acquiring at least one of a heart synchronized signal synchronizing with workings of a heart of the patient and an aspiration synchronized signal synchronizing with aspiration of the patient, when the three-dimensional image data group on the patient is acquired; and detecting an overlapped region of the three-dimensional data acquired by the ultrasonic scanning from different echo windows, for the three dimensional image data group acquired in the same time phase in synchronization with the heart synchronized signal or aspiration synchronized signal;

combining the three-dimensional image data acquired by the ultrasonic scanning from different echo windows, based on the overlapped region;

generating a panorama three-dimensional image data group consisting of panorama three-dimensional image data which are continued in time and have a display area larger than each of the three-dimensional image data;

dividing the overlapped regions in three-dimensional image data, into segments;

acquiring for each divided segment an average luminance of pixel values included in the image data of each echo window within said each divided segment; and selecting based on the average luminance acquired for each divided segment, the image data of only that echo window having a highest average luminance within each said divided segment to be used for the three-dimensional image data adopted for the combining step.

12. An ultrasonic diagnostic apparatus, comprising:
a computer;
a non-transitory computer readable medium storing program instructions which when executed by the computer results in performance of steps comprising,
initiating ultrasonic scanning of the same region in a patient two or more times from different echo windows, so as to overlap at least one part,
acquiring a three-dimensional image data group on the patient, the three-dimensional image data group consisting of three-dimensional image data continued in time by the ultrasonic scanning from the different echo windows,
acquiring at least one of a heart synchronized signal synchronizing with workings of a heart of the patient and an aspiration synchronized signal synchronizing with aspiration of the patient, when the three-dimensional image data group on the patient is acquired,
detecting an overlapped region of the three-dimensional data acquired by the ultrasonic scanning from different echo windows, for the three dimensional image data group acquired in the same time phase in synchronization with the heart synchronized signal or aspiration synchronized signal,
combining the three-dimensional image data acquired by the ultrasonic scanning from different echo windows, based on the overlapped region,
generating a panorama three-dimensional image data group consisting of panorama three-dimensional image data which are continued in time and have a display area larger than each of the three-dimensional image data,
dividing the overlapped regions in three-dimensional image data, into segments;
generating, for each echo window within each said divided segment, a histogram of the frequency of pixel brightness against the number of gray levels in the three-dimensional image data;
setting, for each echo window within each said divided segment, a region corresponding to frequency components higher than a center frequency of each histogram as a specific part, and
comparing the histograms for each echo window within each said divided segment and selecting the three-dimensional image data which includes more frequency components corresponding to the specific part as the three-dimensional image data to be adopted in the combining step.

* * * * *